United States Patent [19]

Nielsen

[11] Patent Number: 4,477,330
[45] Date of Patent: Oct. 16, 1984

[54] ELECTROCHEMICAL ELECTRODE DEVICE

[75] Inventor: Povl H. Nielsen, Bronshoj, Denmark

[73] Assignee: Radiometer A/S, Bronshoj, Denmark

[21] Appl. No.: 426,178

[22] Filed: Sep. 28, 1982

[30] Foreign Application Priority Data

Oct. 1, 1981 [DK] Denmark ............................ 4363/81

[51] Int. Cl.³ ............................................. G01N 27/26
[52] U.S. Cl. ..................................... 204/414; 204/418;
204/419; 204/420; 204/435
[58] Field of Search ............... 204/414, 418, 419, 420,
204/435; 128/635

[56] References Cited

U.S. PATENT DOCUMENTS

| | | | |
|---|---|---|---|
| 2,755,243 | 7/1956 | Beckman et al. | 204/420 |
| 3,145,158 | 8/1964 | Matsuyama | 204/435 |
| 3,434,953 | 3/1969 | Porter | 204/435 |
| 3,463,718 | 8/1969 | Detemple | 204/435 |

Primary Examiner—John F. Niebling
Attorney, Agent, or Firm—Hubbell, Cohen, Stiefel & Gross

[57] ABSTRACT

An electrochemical electrode device comprising a tubular member having a bottom end adapted to be inserted into a liquid sample to be measured, and a top end which is closed by a cap member including electrical conductors by means of which the electrodes of the electrode device are connected to an outer cable. In order to facilitate the introduction of liquid or gel into an inner space defined within the tubular member as well as withdrawal of liquid or gel from that space, a longitudinally extending passage is formed within the cap member. This passage may be selectively opened and closed by means of a closure member which is received in a cavity extending transversely to and intersecting the longitudinal passage. The closure member is preferably in the form of a swingably mounted slide valve member or a rotatable cock member.

14 Claims, 4 Drawing Figures

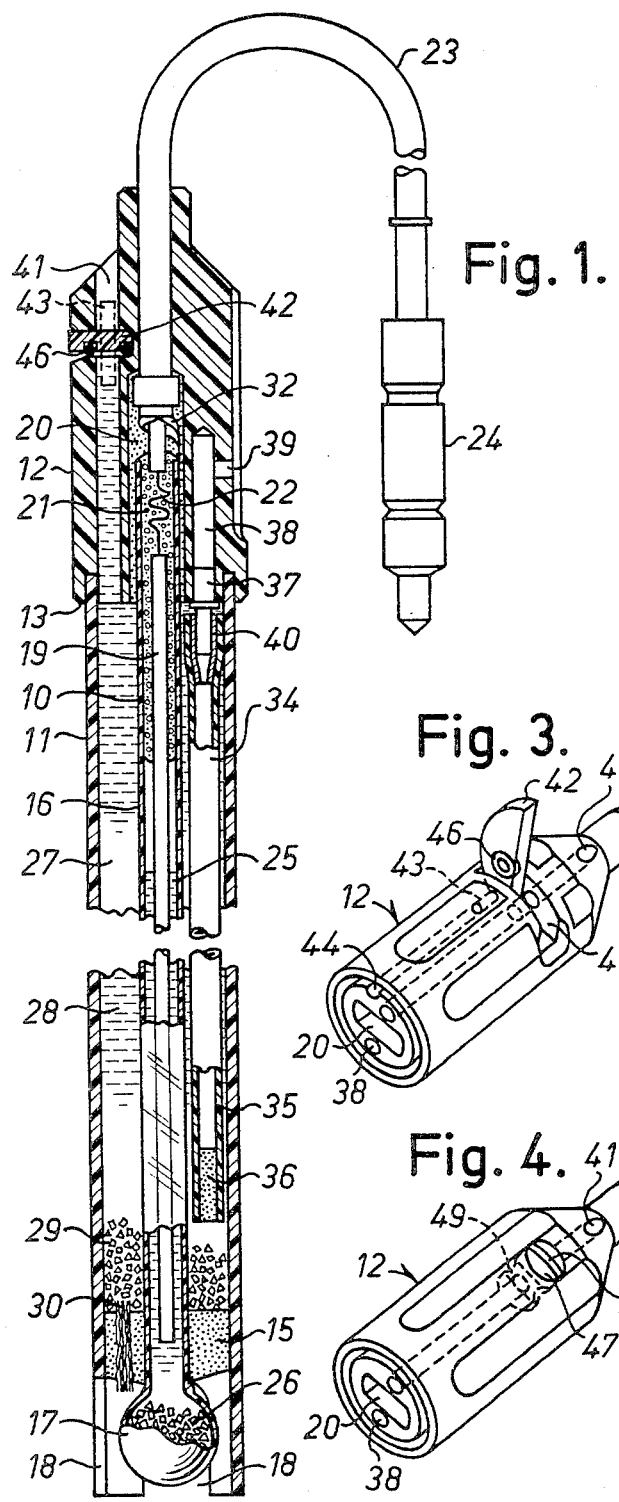

ELECTROCHEMICAL ELECTRODE DEVICE

BACKGROUND OF THE INVENTION

1. Field of the Invention

The present invention relates to an electrochemical electrode device.

Such electrode devices include i.e. electrochemical reference electrode devices and so-called combination electrode devices, the latter comprising in one and the same device a measuring part and a reference part.

2. Description of the Prior Art

Very often such electrochemical electrode devices comprise a tubular member essentially sealed at its bottom end so as to establish a container for an inner liquid. The other end of the tubular member is normally closed by a cap member including means for electrically connecting a reference member arranged within the tubular member, to an external conductor or cable.

As far as reference electrode devices and combination electrode devices are concerned, liquid junction means, i.e. a porous plug, a strand or bundle of fibres, such as glass or plastics fibres, or the like should be provided in the above-mentioned closure for establishing electrical contact between the inner liquid and the liquid into which the electrode device is inserted when used. The inner liquid or salt bridge solution is an electrolyte forming a slat-bridge between the liquid junction and an inner reference member located within said tubular member. Usually, the salt bridge solution is a more or less saturated potassium chloride solution and the viscosity of the salt bridge solution may be adjusted by means of gelation agents.

In some cases, it is preferred to use a salt bridge liquid having such low visocity that the liquid may seep through the liquid junction means, whereby a self-cleaning effect of the liquid junction means is obtained. In other cases it is desirable to use a more viscous salt bridge liquid or gel so as to prevent the sample being measured from contamination by seeping salt bridge liquid.

In known electrochemical electrode devices of the type described above, the upper part of the cylindrical wall of the tubular member may be provided with a refill opening which is closed by means of a removable resilient plug extending radially outwardly from the outer cylindrical surface of the tubular member, a rubber hose surrounding the tubular member and being slidable in the axial direction thereof, or the like. This opening makes it possible to refill the tubular member with salt solution so as to replace solution in the tubular member with a different type, for example a more viscous liquid or a gel.

When the refill opening is defined in the cylindrical wall of the tubular member, it may be difficult to completely fill the inner space of the tubular member with liquid or gel, while the electrode device is held in its upright measuring position. The consequent air volume within the tubular member may cause a certain "noise" which may interfere with the potential obtained by the electrode device. Normally, the cap member surrounds the adjacent end of the tubular member so as to form an annular abutment shoulder. The tubular member of the electrode device may then be inserted through an opening in a horizontal wall or panel and be retained in position—for example its measuring or storage position—by engagement between the annular shoulder and the upper surface of the wall or panel. However, a removable stopper projecting radially outwardly from the tubular may interfere with the insertion of the tubular member through the opening defined in the said panel or wall. Furthermore, a refill opening defined in the cylindrical wall of the tubular member does not make it possible to introduce liquid or gel into and/or remove liquid or gel from the electrode device while the device is in an upright position of use.

U.S. Pat. Nos. 3,145,158 and 3,434,953 disclose electrochemical electrode devices in which a refill passage is formed in a cap member closing the upper end of a tubular member. The refill passage extends from an enlarged opening in an upper surface part of the cap member to the inner space of the tubular member. The enlarged opening of the passage is then closed by means of a removable stopper extending from the upper surface part of the cap member, or the enlarged opening may have internal threads which may cooperate with the threads of a screw serving as a removable closure member.

SUMMARY OF THE INVENTION

The present invention provides an electrochemical electrode device of the above type which is more convenient in structure and use than the known electrode described above.

Thus, the electrode device according to the invention comprises a tubular member, sealing means substantially sealing a bottom end of the tubular member, a cap member closing an upper end of the tubular member so as to define an inner space therein for containing a liquid or gel, said cap member defining a passage communicating the inner space of the tubular member with an opening in an upper surface part of the cap member, and a closure member being received in a cavity defined in the cap member and intersecting the passage therein, the closure member being selectively movable between opening and closing positions, in which communication between the inner space of the tubular member and the ambient atmosphere through said passage is established and interrupted, respectively.

Liquid or gel is normally introduced into and removed from the inner space of a tubular member by means of a syringe or the like having a cannula or spout which may be inserted into the passage opening defined in the upper surface part of the cap member. In the electrode device according to the invention where the closure member is adapted to block the passage at a location between the end of the passage, it is possible to insert a cannula or spout into the upper opening, before the closure member is moved to its open position, if desired. Furthermore, the intersecting cavity may be sized so as to completely receive the closure member in its closed position, so that the risk that the closure member may inadvertently be moved to its opening position, is substantially reduced.

The said closure member may be of any suitable type. However, in one preferred embodiment the closure member is a cock member arranged rotatably within the cavity, so that the cock member may be rotated between opening and closing positions. The rotatable cock member may, for example, have an exposed outer end comprising a slot or another recess which may cooperate with a screw driver, a wrench or a similar tool. In a second, still more preferred embodiment the closure member is a slide valve member slidably mounted within the cavity. The slide valve member may be a substantially plane member slidably mounted within a slot-like cavity, and at least one of the opposite surfaces of the plane member may then have a resilient sealing member, such as a sealing ring, mounted thereon. The sealing member may then project slightly from said surface or surfaces so as to cover or encircle the adjacent cross-section of the passage in the closing position of the slide valve member. Alternatively, the the sealing ring may be mounted stationarily on one of the surface parts defining the cavity and facing the plane member.

In its closing position the slide valve member is preferably positioned completely within the confines of the cap member, while it may project from the outer peripheral surface of the cap member in the opening position of the slide valve member. The slide valve member may be movable along a straight or linear path. However, in the preferred embodiment the slide member is swingably mounted. The slide valve member may then be moved between its opening and closing positions without being separated from the cap member.

In principle, the passage defined in the cap member may have any suitable shape or course, including straight, curved, edged, and tortuous courses. However, in the preferred embodiment the passage extends substantially linearly through the cap member in and substantially in the axial direction of the tubular member. It is then possible to introduce liquid or gel into and to remove liquid or gel from the inner space of the tubular member by means of a syringe having a cannula or spout which may be inserted through the longitudinally extending passage and into the inner space of the tubular member.

BRIEF DESCRIPTION OF THE DRAWINGS

The invention will now be further described with reference to the drawing wherein FIG. 1 is a side view and partially sectional view of an embodiment of the electrode device according to the invention, FIG. 2 is a similar view as that shown in FIG. 1, the sectional plane in FIG. 2 forming right angles with that of FIG. 1, FIG. 3 is a perspective view of a first embodiment of a cap member of the electrode device shown in FIGS. 1 and 2, and FIG. 4 is a second embodiment of the cap member.

DESCRIPTION OF THE PREFERRED EMBODIMENTS

The electrochemical electrode device shown in FIGS. 1 and 2 is of the combination electrode type and comprises a measuring part 10 extending axially within a tubular member 11. The upper end of the tubular member 11 is closed by a cap member 12 having an annular channel formed in its bottom end surface for receiving the upper end portion of the tubular member 11, so that an annular shoulder 13 is formed by the part of the bottom end surface of the cap member 12 located outside said channel. The annular space defined between the inner surface of the tubular member 11 and the bottom end part of the measuring part 10 is closed by a sealing mass 15, which is preferably silicone rubber. The measuring part 10 comprises a glass tube 16 having a bulb 17 formed at its lower free end. This bulb 17 which is arranged outside the sealing mass 15, but positioned within and protected by the lower end of the tubular member 11, is made from a pH-sensitive glass membrane. Cut outs 18 in the lower end portion of the tubular member 11 secure that the bulb 17 is exposed to a sample liquid contained in a sample container, when the lower end of the electrode device is placed within that container.

The measuring part 10 also includes an internal reference member 19 which comprises an Ag/AgCl electrode of the type disclosed in U.S. Pat. No. 3,676,319, and which extends axially within the glass tube 16. The upper end of the glass tube 16 is received within an axial bore 20, and the upper end of the tube 16 as well as the bore 20 are filled with a sealing mass 21. At its upper end the silver conductor of the internal reference member 19 is connected to a wire or conductor 22 forming part of a cable 23. One end of the cable 23 extends axially through the cap member 12, while the other end of the cable is connected to a plug 24. The bulb 17 and a substantial part of the glass tube 16 are filled with a pH-buffer solution further comprising a saturated solution of potassium chloride, and the bulb 17 contains non-dissolved crystals 26 of that substance. The annular space 27 defined between the glass tube 16 and the tubular member 11, which is preferably made from plastic, is filled with a saturated solution of potassium chloride 28 containing non-dissolved crystals. A liquid junction member 30, which may, for example, be in the form of a fibre wick or a porous plug 30, which is preferably of a ceramic material, extends axially through the sealing mass 15, so that its outer end may be exposed to a sample in which the lower end of the electrode is inserted. The annular space 27 also contains an outer reference member 31 which preferably comprises an Ag/AgCl electrode of the type disclosed in U.S. Pat. No. 3,676,319. The silver conductor of member 31 is connected to a conductor forming a shield 32 of the cable 23, by means of a wire 33. The space 27 also contains a pressure balancing device 34 which comprises an elastic, compressible tube, for example of rubber, closed at the lower end by means of a plug 36 of glue or another sealing mass. One end of a tube connector 37 is inserted in an axial bore 38 in the cap member 12, and this bore communicates with the atmosphere through a transverse bore 39. The upper end of the compressible tube 35 is surrounding the other end of the tube connector 37 and fastened thereto, for example by glue 40. It is understood that the inner space of the compressible tube 35 is always in communication with the ambient atmosphere so that the pressure within the space 27 will always substantially correspond to the ambient pressure, even when the space 27 is sealed therefrom, unless the tube of the device 34 is totally compressed. Hereby, pressure variations inside the electrode device due to variations in the volume of the inner liquid occurring e.g. when the electrode device is subjected to temperature variations, is avoided.

As far as described up till now, the electrode device shown in FIGS. 1 and 2 is substantially known as far as structure as well as function are concerned. Therefore it has not been deemed necessary to further describe the function of the electrode device.

The novel features of the electrode device shown on the drawing reside in the cap member 12. This cap member defines a passage or bore 41 therethrough which preferably extends axially from the top of the cap member to the bottom surface thereof defining the upper end of the annular space 27. FIG. 3 shows an embodiment in which the passage or bore 41 in the cap member 12 may be closed by means of a slide valve member 42 mounted swingably about a pin 43 arranged within an axial bore 44. The valve member 42 is mounted in a transverse slot 45 intersecting the passage 41, and the valve member is mounted so as to be movable between a closing position in which the valve member is fully received within the slot so as to close the passage 41, and an opening position, in which the valve member 42 projects from the contour of the cap member 12 and leaves the passage 41 open as shown in FIG. 3. In the embodiment shown in FIGS. 1-3 a sealing ring 46 is mounted on at least the bottom surface of the valve member 42 so that the sealing ring 46 surrounds the passage or bore 41 in the closing position of the valve member 42 so as to obtain a good sealing effect. The sealing ring 46 may, of course, be replaced by any other suitable sealing member, such as a sealing disc. Alternatively, the sealing member or sealing ring 46 may be mounted stationarily on one or both of the parallel surface parts defining the slot 45, so as to encircle the passage 41 and sealingly cooperate with the valve member 42.

If the annular space 27 is to be refilled with liquid, or the liquid 28 therein is to be removed or replaced by another liquid, the valve member 42 is moved to its opening position shown in FIG. 3, whereafter a cannula or spout forming part of some type of a syringe may be inserted through the axial passage 41 and into the annular space 27. If desired, the tip of the cannula or spout may be moved right to the bottom of the annular space 27, so that all of the liquid 28 may be removed, if desired. Removal and/or introduction of liquid may conveniently take place when the measuring electrode is placed in an upright measuring position as shown in FIGS. 1 and 2. For example, the tubular member 11 may be inserted through an opening in a horizontal wall or panel (not shown), and the shoulder 13 may then engage with the upper surface of the panel.

FIG. 4 shows an alternative embodiment of the cap member 12, where the transversely swingable valve member 42 has been replaced by a rotatable cock member 47. The outer end of this cock member is provided with a slot 48, so that the cock member 47 may be rotated, for example by means of a screw driver, between a closing position, in which the bore 41 is closed by the cock member, and an opening position in which a bore 49 of the cock member is aligned with the passage or bore 41.

It should be understood that various amendments and modifications of the embodiment shown on the drawing could be made without departing from the scope of the present invention. Thus, the valve member 42 and the cock member 47 could be replaced by any other type of suitable closing members. It should also be understood that the cap member 12 could be used in connection with other types of electrode devices in which a liquid or gel must be inserted and/or removed from time to time.

I claim:

1. An electrochemical electrode device comprising a tubular member having a bottom end and an upper end, a sealing means substantially sealing the bottom end of the tubular member, a cap member closing the upper end of the tubular member so as to define an inner space therein for containing a liquid or a gel, said cap member having a passage connecting the inner space of the tubular member with the outside atmosphere, said passage having an inner end opening and an outer end opening said outer end opening being located in the upper surface part of the cap member, and a closure member being received in a cavity defined in the cap member and intersecting the passage therein at a point between the inner end opening and the outer end opening of the passage, the closure member being selectively movable between open and closed positions, whereby communication between the inner space of the tubular member and the ambient atmosphere through said passage is established and interrupted, respectively.

2. An electrode device according to claim 1, wherein the closure member is a cock member arranged rotatably within the cavity and containing a bore which may be aligned with the passage in the cap member.

3. An electrode device according to claim 1, wherein the closure member is a slide valve member slidably mounted within the cavity.

4. An electrode device according to claim 3, further comprising a resilient sealing member mounted on a surface part of the slide valve member so as to project slightly from this surface part and so as to cover the adjacent cross-section of the passage in the closed position of the slide valve member.

5. An electrode device according to claim 4, wherein the sealing member is a sealing ring encircling the cross-section of said passage.

6. An electrode device according to claim 3, wherein a resilient sealing ring is mounted on the cavity surface part intersected by the passage so as to project slightly from the cavity surface part and so as to encircle the opening of the longitudinal passage into the cavity surface part.

7. An electrode device according to claim 3, wherein the slide valve member is a plate member having opposite, substantially plane side surfaces for cooperating sealingly with spaced, substantially parallel inner surface parts of the cavity which is slot-like and extends transversely into the passage.

8. An electrode device according to any of the claims 3 to 7, wherein the slide valve member is swingably mounted.

9. An electrode device according to claim 1, wherein the passage extends substantially linearly through the cap member and substantially in the axial direction of the tubular member.

10. An electrochemical electrode device comprising a tubular member having a bottom end and an upper end, sealing means substantially sealing the bottom end of the tubular member, at least one reference member arranged within the tubular member, a cap member closing the upper end of the tubular member so as to define an inner space therein for containing a liquid or a gel, said cap member including means for electrically connecting the reference member with an external cable and having a passage connecting the inner space of the tubular member with the outside atmosphere, said passage having an inner end opening and an outer end opening, said outer end opening being located in the upper surface part of the cap member, and a closure member being received in a cavity defined in the cap member and intersecting the passage therein at a point between the inner end opening and the outer end opening of the passage, the closure member being selectively movable between open and closed positions, whereby communication between the inner space of the tubular member and the ambient atmosphere through said passage is established and interrupted, respectively.

11. An electrode device according to claim 10, wherein the closure member is a cock member arranged rotatably within the cavity and containing a bore which may be aligned with the passage in the cap member.

12. An electrode device according to claim 11, further comprising a resilient sealing ring mounted on a surface part of the slide valve member so as to project slightly from this surface part and so as to encircle the adjacent cross-section of the passage in the closed position of the slide valve member.

13. An electrode device according to claim 11, wherein the slide valve member is a plate member having opposite, substantially plane surfaces for cooperating sealingly with spaced, substantially parallel inner surface parts of the cavity, which is slot-like and extends transversely into the passage.

14. An electrode device according to claim 13, wherein the slide valve member is mounted so as to be swingable between its open and closed position.

* * * * *